United States Patent [19]

Audegond et al.

[11] Patent Number: 5,435,992
[45] Date of Patent: Jul. 25, 1995

[54] NON-IRRITATING PESTICIDAL COMPOSITIONS

[75] Inventors: Lilian Audegond, Enghien Les Bains, France; Bernard Lambert, London, England

[73] Assignee: Roussel Uclaf, France

[21] Appl. No.: 41,843

[22] Filed: Apr. 2, 1993

[30] Foreign Application Priority Data

Apr. 9, 1992 [FR] France ................................ 92 04347

[51] Int. Cl.$^6$ ..................... A61K 49/00; A01N 37/34; A01N 43/38; A01N 53/00
[52] U.S. Cl. ................................. 514/419; 514/461; 514/521; 514/531; 514/974
[58] Field of Search ............... 514/521, 531, 419, 461; 424/10

[56] References Cited

U.S. PATENT DOCUMENTS

| Re. 31,927 | 6/1985 | Coffee et al. | 514/521 |
| 4,871,766 | 10/1989 | Tsuda et al. | 514/521 |
| 5,300,520 | 4/1994 | Igarashi et al. | 514/367 |

FOREIGN PATENT DOCUMENTS 0001454  4/1979  European Pat. Off. .

*Primary Examiner*—Allen J. Robinson
*Attorney, Agent, or Firm*—Bierman and Muserlian

[57] ABSTRACT

Pesticidal compositions comprising a pesticidally effective amount of at least one pyrethrinoid, a biphenyl aromatic solvent and optionally a mineral, vegetable or transesterified vegetable oil and a method of combatting pests.

18 Claims, No Drawings

NON-IRRITATING PESTICIDAL COMPOSITIONS

Pyrethrinoids are widely used in the agricultural domain, for combatting parasites of vegetation and parasites of the soil, in the domain of domestic and public hygiene, for combatting particularly parasites of premises, of food stores, of wood and of residential areas, as well as in the anti-parasitic treatment of man and animals. Pyrethrinoids are increasingly being used as they are remarkably efficient and allow particularly the combatting of parasites, while respecting the environment. Nevertheless, pyrethrinoids sometimes have the disadvantage of causing irritation, which can make their use somewhat unpleasant in premises for example.

OBJECTS OF THE INVENTION

It is an object of the invention to provide novel non-irritating pyrethrinoid compositions with a reduced odor.

It is another object of the invention to provide an improved method of combatting pests.

These and other objects and advantages of the invention will become obvious from the following detailed description.

THE INVENTION

The novel non-irritating pesticidal compositions of the invention with a reduced smell are comprised of a pesticidally effective amount of at least one pyrethrinoid, a biphenyl aromatic solvent and optionally a mineral, vegetable or transesterified vegetable oil.

The compositions of the invention have a much lower capacity for irritation than that of the compositions currently available on the market, as is shown by the results of the tests described in detail hereafter, in the experimental part. The compositions also have the advantage of greatly reducing the unpleasant smell due to the standard aromatic solvents used, which is very useful during air and surface treatment for combatting termites, for example.

The compositions of the invention are therefore particularly suitable for surface treatments for flying insects such as flies and mosquitoes, and crawling insects such as cockroaches, lice, fleas and ants, as well as for combating wood parasites. The compositions are also used for killing the flying or crawling insects mentioned above in the form of an outside air treatment for urban areas, as well as in the form of an air treatment inside buildings or houses.

The pesticide compositions preferably have at least one aromatic solvent of the formula

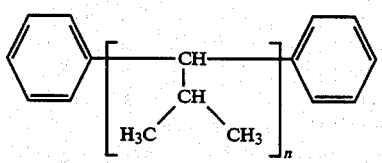

wherein n is 0 or 1 and the phenyl is optionally substituted by at least one alkyl of 1 to 8 carbon atoms. When the phenyls are substituted by one or more alkyls, it is preferably one or more methyl, ethyl, n-propyl, isopropyl or n-butyl in the ortho, meta and/or para positions on the phenyl nuclei.

The preferred pesticide compositions are those in which the aromatic solvent is a BVA XK solvent or a mixture of BVA XK solvents. The BVA XK solvents, and particularly BVA XK$_3$, (alkylbiphenyl mixture) BVA XK$_{20}$, BVA XK$_{25}$, BVA XK$_{29}$ (mono and dialkylated biphenyls) and BVA XK$_{32}$ solvents, are solvents containing biphenyl compounds or mixtures of biphenyl compounds sold by the firm BVA OILS. Preferred as the aromatic solvent is a BVA XK$_3$ solvent.

The aromatic solvent may also be a dibenzyltoluene, for example those in which the aromatic solvent is MARLOTHERM.S sold by EXXON Chemicals which is a mixture of dibenzyltoluene isomers.

Preferably, the pesticide compositions of the invention contain in addition a vegetable, mineral or transesterified vegetable oil. The vegetable oil can be of a very varied origin. It may be, for example, an oil from cotton, sunflower, soya, rape or corn, preferably a cotton oil, or also a methylated rape oil.

The pyrethrinoids used are products which are known and widely described in the literature such as permethrin, deltamethrin, tetramethrin, cypermethrin and the various mixtures of isomers which result from it, and notably α-cypermethrin and asymethrin, esbiothrin, kadethrin, acrinathrin, cyhalothrin and the various mixtures of isomers which result from it, and especially λ-cyhalothrin, cyfluthrin, tralomethrin, fluvalinate, fenvalerate, S-fenvalerate or (S) ā-cyano 3-phenoxy benzyl (1R, cis) 2,2-dimethyl 3-[(Z) 2-(methoxycarbonyl) ethenyl] cyclopropane carboxylate.

The compositions of the invention can contain any pyrethrinoid, but are naturally of greater use when the pyrethrinoid or pyrethrinoids contained have a capacity for irritation sufficiently high to be a nuisance to the user, preferably deltamethrin.

More preferred compositions of the invention are the compositions containing 1 to 100 g/l of pyrethrinoid and 300 to 900 g/l of the biphenyl aromatic solvent.

More preferred are pesticide compositions containing 200 to 800 g/l of vegetable oil and 300 to 500 g/l of biphenyl aromatic solvent.

The compositions of the invention can contain in addition a non-ionic surfactant such as Arkopal NO 40 (polyglycol ethers of nonylphenol (an alkylphenylpolyglycol) and/or Emulsogen EL (polyglycol esters of fatty acids (a fatty acid polyglycolester) both marketed by HOECHST.

The compositions of the invention can be presented in the usual forms of the agrochemical industry or the veterinary industry for combatting external parasites of animals, of insect and acarid type, using baths, aerosols or according to the so-called "pour on" method. They can also be used in shampoos, lotions or creams for combatting lice in man, for example. Preferred compositions are presented in the form of emulsifiable concentrates or ready-to-use solutions of ULV type or concentrates for dilution.

Among the preferred compositions of the invention are those that contain in addition 100 to 200 g/l of cyclohexanone or another optional solvent of the ketone or glycol ether type such as N-methyl pyrrolidone, N-amylketone or propyleneglycol methyl ether. More preferred compositions of the invention are those that contain 12 to 18 g/l of deltamethrin, notably those that contain 250 to 350 g/l of cotton oil and 250 to 500 g/l of BVA XK$_3$ solvent. Among the latter, there can be mentioned those that contain in addition 0.1 to 10 g/l of BHT or 2,6 bis (1,1-dimethyl)-ethyl-4-methylphenol, 10 to 50 g/l of calcium phenylsulfonate, 10 to 20 g/l of Emulsogen EL 360, 30 to 70 g/l of Arkopal N 0 40.

The compositions of the invention can contain one or more pyrethrinoids as well as other insecticide products such as organo-phosphorated compounds, organo-chlorinated compounds, carbamates as well as other acaricide products, fungicides and herbicides. The compositions of the invention can also contain one or more synergists for pyrethrinoids such as piperonyl butoxide or the MGK 264$^R$ for example.

The novel method of the invention for combatting pests comprises contacting pests with a pesticidally effective amount of a composition comprising a pesticidally effective amount of at least one pyrethrinoid, a biphenyl aromatic solvent and optionally a mineral, vegetable or transesterified vegetable oil. The pests are preferably insects.

In the following examples, there are described several preferred embodiments to illustrate the invention. However, it is to be understood that the invention is not intended to be limited to the specific embodiments.

EXAMPLE 1

The following components were admixed:

| RAW MATERIALS | IN G/L |
| --- | --- |
| Technical deltamethrin | approx. 15 |
| BHT or 2,6-bis (1,1-dimethyl) ethyl-4-methyl phenol | approx. 1 |
| Calcium phenylsulfonate | approx. 30 |
| Emulsogen EL 360 ® (HOECHST) | approx. 20 |
| Arkopal N 040 ® (HOECHST) | approx. 50 |
| Cyclohexanone | approx. 150 |
| Cotton oil | approx. 300 |
| BVA XK$_3$ ® (BVA oils) | approx. 388.59 |
| Acetic acid | approx. 0.1 |

The compositions were used diluted in water and were applied with a sprayer. 100 ml of this composition can for example be diluted in 5 liters of water whereby 100 m$^2$ of surface area can be effectively treated (treatment against crawling insects). When it is desired to treat surfaces against flying insects, 65 ml of the composition can be diluted in 5 liters of water.

When it is desired to carry out special treatments, 0.7 liters of the composition can be diluted in 8 to 10 liters of petroleum solvent and the solution obtained can be applied at the rate of 0.5 liters of solution per hectare. When it is desired to treat interior spaces, 0.5 liters to 1 liter of the composition can be diluted with 3 to 5 liters of petroleum solvent and 0.25 liters of the solution can be applied to treat 1000 m$^3$ of interior space.

EXAMPLE 2

An emulsifiable concentrate was prepared containing the following components:

| RAW MATERIALS | IN G/L |
| --- | --- |
| Tralomethrin | approx. 144 |
| BHT | 1 |
| Calcium phenylsulfonate | 35 |
| Emulsogen EL 360 ® | 35 |
| Arkopal N 040 ® | 31 |
| Cyclohexanone | 150 |
| Cotton oil | 300 |
| BVA XK$_3$ | 400 |
| Acetic acid | 0.1 |

EXAMPLE 3

An emulsifiable concentrate was prepared containing the following components:

| RAW MATERIALS | IN G/L |
| --- | --- |
| Cyalothrin | 15 |
| BHT | 1 |
| Calcium phenylsulfonate | 35 |
| Emulsogen EL 360 | 35 |
| BVA XK$_3$ ® | approx. 390 |
| Cyclohexanone | 150 |
| Cotton oil | 300 |

EXAMPLE 4

An emulsifiable concentrate was prepared containing the following components:

| RAW MATERIALS | IN G/L |
| --- | --- |
| Acrynathrin | 30.6 |
| BHT | 1 |
| Calcium phenylsulfonate | 35 |
| Emulsogen EL 360 ® | 35 |
| BVA XK$_3$ ® | 403 |
| Cyclohexanone | 150 |
| Acetic acid | 0.1 |
| Cotton oil | 300 |

EXAMPLE 5

An emulsifiable concentrate was prepared containing the following components:

| RAW MATERIALS | IN G/L |
| --- | --- |
| Deltamethrin | approx. 15 |
| BHT | 1 |
| Acetic acid | 0.1 |
| Calcium phenylsulfonate | 50 |
| Emulsogen EL 360 ® | 20 |
| BVA XK$_3$ ® | 730 |
| Cyclohexanone | 50 |

EXAMPLE 6

An emulsifiable concentrate was prepared containing the following components:

| RAW MATERIALS | IN G/L |
| --- | --- |
| 98% technical tralomethrin | 144 |
| BHT | 1 |
| Calcium phenylsulfonate | 35 |
| Emulsogen EL 360 | 35 |
| Arkopal N 040 | |
| Cyclohexanone | |
| Cotton oil | |
| BVA XK3 | 755 |
| Acetic acid | 0.1 |

EXAMPLE 7

An emulsifiable concentrate was prepared containing the following components:

| RAW MATERIALS | IN G/L |
| --- | --- |
| Cyfluthrin | 15 |
| BHT | 1 |
| Calcium phenylsulfonate | 35 |

| RAW MATERIALS | IN G/L |
|---|---|
| Emulsogen EL 360 | 35 |
| Cyclohexanone | 15 |
| Cotton oil | 300 |
| Acetic acid | 0.1 |

EXAMPLE 8

An emulsifiable concentrate was prepared containing the following components:

| RAW MATERIALS | IN G/L |
|---|---|
| Cypermethrin | 65.900 |
| BHT | 1 |
| Calcium phenylsulfonate | 30 |
| Emulsogen EL 360 | 20 |
| Arkopal N 040 | 50 |
| Cyclohexanone | 150 |
| Cotton oil | 300 |
| BVA XK3 | 37 |

EXAMPLE 9

An emulsifiable concentrate was prepared containing the following components:

| RAW MATERIALS | IN G/L |
|---|---|
| Permethrin | 159.600 |
| BHT | 1 |
| Calcium phenylsulfonate | 30 |
| Emulsogen EL 360 | 20 |
| Cyclohexanone | 150 |
| Cotton oil | 300 |
| BVA XK3 | 273 |

EXAMPLES 10 to 14

Compositions similar to Example 1 were prepared in which the 300 g of cotton oil was replaced by 300 g of white paraffin oil, 300 g of rape oil, 300 g of soya oil, 300 g of sunflower oil or 300 g of methylated rape oil.

EXAMPLES 15 to 20

Compositions similar to those of Examples 1 and 10 to 14 were prepared in which deltamethrin was replaced by (S) α-cyano 3-phenoxy benzyl (1R,cis) 2,2-dimethyl 3-[(Z) 2-(methoxycarbonyl) ethenyl] cyclopropane carboxylate or the product of Example 1 of French Patent No. 2,480,748.

Study of the irritative effect of the compositions of the invention:

The irritative effect of the products was studied in male guinea pigs weighing approximately 300 g and the test used is an inhalation test. The nebulization of the products was carried out using a medical-type ultrasonic nebulizer producing a mist composed of particles of 0.5 to 5 microns.

The following compositions were studied: a composition of 15 g/liter of deltamethrin in SOLVESSO, a composition of 15 g/l of deltamethrin in BVA XK3 ® solvent (composition of Example 5), a composition of 15 g/l of deltamethrin in a mixture of BVA XK3 solvents and cotton oil (composition of Example 1).

The guinea pigs were placed individually in a cage through which the aerosol produced by the nebulizer circulated. The number of coughs over 5 minutes were counted for each guinea pig and the average number of coughs for 6 animals was calculated. The results expressed as the number of coughs over 5 minutes were as follows:

| Test 1/ Deltamethrin in Solvesso ® | | | |
|---|---|---|---|
| Number of coughs over 5 minutes | | | |
| mg of deltamethrin/l | 18.75 | 37.5 | 75 |
| ml of formulation/l of water | 1.25 | 2.5 | 5.00 |
| 1 | 0.00 | 1.00 | 19.00 |
| 2 | 1.00 | 4.00 | 35.00 |
| 3 | 0.00 | 5.00 | 23.00 |
| 4 | 2.00 | 6.00 | 18.00 |
| 5 | 2.00 | 47.00 | 33.00 |
| 6 | 4.00 | 2.00 | 24.00 |
| 7 | | | |
| 8 Average | 1.50 | 10.83 | 25.33 |
| 9 Standard deviation | 1.52 | 17.81 | 7.12 |
| 10 Average vol. nebulized in ml | 7.00 | 7.00 | 4.00 |

| Test 2/ Deltamethrin CE 15 in the BVA composition of Example 5 | | |
|---|---|---|
| Number of coughs over 5 minutes | | |
| mg of deltamethrin/l | 75 | 150 |
| ml of formulation/l of water | 5 | 10 |
| 1 | 3.00 | 1.00 |
| 2 | 1.00 | 6.00 |
| 3 | 1.00 | 3.00 |
| 4 | 0.00 | 2.00 |
| 5 | 0.00 | 21.00 |
| 6 | 1.00 | 2.00 |
| 7 | | |
| 8 Average | 1.00 | 5.83 |
| 9 Standard deviation | 1.10 | 7.63 |
| 10 Average vol. nebulized in ml | 6.00 | 6.00 |

| Test 3/ Deltamethrin CE 15 in BVA XK3 ® + cotton oil Composition of Example 1 | | |
|---|---|---|
| Number of coughs over 5 minutes | | |
| mg of deltamethrin/l | 75 | 150 |
| ml of formulation/l of water | 5 | 10 |
| 1 | 0.00 | 0.00 |
| 2 | 0.00 | 4.00 |
| 3 | 0.00 | 2.00 |
| 4 | 1.00 | 0.00 |
| 5 | 3.00 | 0.00 |
| 6 | 0.00 | 2.00 |
| 7 | | |
| 8 Average | 0.67 | 1.33 |
| 9 Standard deviation | 1.21 | 1.63 |
| 10 Average vol. nebulized in ml | 6.00 | 6.00 |

Conclusion

For the same concentration of active ingredient, (75 mg of deltamethrin/l), the compositions of the invention (assayed in tests 2 and 3 above) were much less irritating than the composition assayed in test 1 (deltamethrin in Solvesso), 25 coughs over 5 minutes for the latter composition and 1 cough or less over 5 minutes for the compositions of the invention. The compositions of the invention were much less irritating than the formulations in SOLVESSO.

At a dose of 150 mg/l, the compositions of Example 1 are significantly less irritating than the compositions of Example 5. The oil reinforced the anti-irratitive effect of the BVA XK3 ® solvent.

Various modifications of the compositions and method of the invention may be made without departing from the spirit or scope thereof and it should be understood that the invention is intended to be limited only as defined in the appended claims.

We claim:

1. Pesticidal compositions consisting essentially of a pesticidally effective amount of at least one pyrethrinoid selected from the group consisting of permethrin, deltamethrin, tetramethrin, cypermethrin, α-cypermethrin, asymethrin, esbiothrin, kadethrin, acrinathrin, cyhalothrin, λ-cyhalothrin, cyfluthrin, tralomethrin, fluvalinate, fenvalerate, S-fenvalerate and (S) α-cyano-3-phenoxy-benzyl (1R,cis) 2,2-dimethyl-3-[(Z)2-(methoxy-carbonyl)-ethenyl]-cyclopropane carboxylate, a biphenyl aromatic solvent selected from the group consisting of dibenzyltoluene and at least one compound of the formula

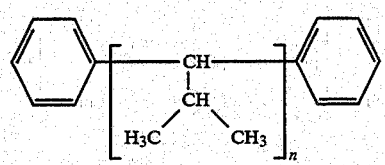

wherein n is 0 to 1 and the phenyl are optionally substituted by at least one alkyl of 1 to 8 carbon atoms and optionally a mineral, vegetable or transesterified vegetable oil.

2. A composition of claim 1 wherein the biphenyl aromatic solvent is at least one compound of the formula

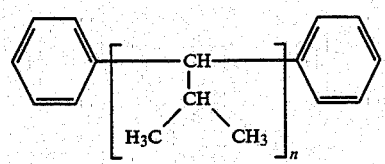

wherein n is 0 to 1 and the phenyl are optionally substituted by at least one alkyl of 1 to 8 carbon atoms and optionally a mineral, vegetable or transesterified vegetable oil.

3. A composition of claim 1 wherein the biphenyl aromatic solvent is a dibenzyltoluene.

4. A composition of claim 1 containing a vegetable, mineral or transesterified vegetable oil.

5. A composition of claim 4 wherein the oil is selected from the group consisting of cotton oil, paraffin oil, soya oil, rape oil, corn oil and methylated rape oil.

6. A composition of claim 4 wherein the oil is cotton oil.

7. A composition of claim 1 wherein the pyrethrinoid is deltamethrin.

8. A composition of claim 1 containing 1 to 100 g/l of the pyrethrinoid.

9. A composition of claim 8 containing 300 to 900 g/l of the biphenyl aromatic solvent.

10. A composition of claim 8 containing 200 to 800 g/l of oil and 300 to 500 g/l of biphenyl aromatic solvent.

11. A composition of claim 1 in the form of an emulsifiable concentrate.

12. A composition of claim 1 also containing 100 to 200 g/l of cyclohexanone.

13. A composition of claim 1 containing 12 to 18 g/l of deltamethrin.

14. A composition of claim 13 containing 250 to 350 g/l of cotton oil and 250 to 500 g/l of biphenyl aromatic solvent.

15. A method of combatting insects comprising contacting insects with an insecticidally effective amount of a composition of claim 1.

16. A method of claim 15 wherein the biphenyl aromatic solvent is at least one compound of the formula

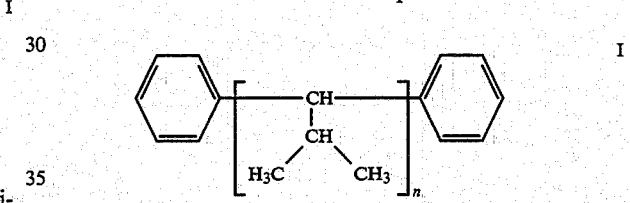

wherein n is 0 to 1 and the phenyls are optionally substituted by at least one alkyl of 1 to 8 carbon atoms.

17. A method of claim 15 wherein the biphenyl aromatic solvent is a dibenzyltoluene.

18. A method of claim 15 containing a vegetable, mineral or transesterified vegetable oil.

* * * * *